(12) United States Patent
Jones

(10) Patent No.: US 11,452,508 B2
(45) Date of Patent: Sep. 27, 2022

(54) BIODEGRADABLE URINE COLLECTOR

(71) Applicant: Abigail Ford Jones, Tuscaloosa, AL (US)

(72) Inventor: Abigail Ford Jones, Tuscaloosa, AL (US)

(*) Notice: Subject to any disclaimer, the term of this patent is extended or adjusted under 35 U.S.C. 154(b) by 202 days.

(21) Appl. No.: 17/064,228

(22) Filed: Oct. 6, 2020

(65) Prior Publication Data
US 2021/0015468 A1 Jan. 21, 2021

Related U.S. Application Data

(63) Continuation-in-part of application No. 16/657,809, filed on Oct. 18, 2019.

(60) Provisional application No. 62/747,279, filed on Oct. 18, 2018.

(51) Int. Cl.
| | |
|---|---|
| *A61B 10/00* | (2006.01) |
| *B67C 11/00* | (2006.01) |
| *C08L 101/16* | (2006.01) |
| *G01N 33/493* | (2006.01) |

(52) U.S. Cl.
CPC ............ *A61B 10/007* (2013.01); *B67C 11/00* (2013.01); *C08L 101/16* (2013.01); *G01N 33/493* (2013.01)

(58) Field of Classification Search
CPC ..... G01N 33/493; C08L 101/16; B67C 11/00; A61B 10/007
USPC ............................................ 141/99, 360, 337
See application file for complete search history.

(56) References Cited

U.S. PATENT DOCUMENTS

| | | | |
|---|---|---|---|
| 3,161,891 A | 12/1964 | Bauman | |
| 3,711,871 A | 1/1973 | Sherin | |
| 3,811,136 A | 5/1974 | Whitney et al. | |
| 4,194,508 A | 3/1980 | Anderson | |
| D274,469 S | 6/1984 | Huang et al. | |
| 4,936,838 A | 6/1990 | Cross et al. | |
| D341,421 S | 11/1993 | Jones | |
| 5,445,292 A * | 8/1995 | Slomski | A61B 10/007 220/834 |
| 5,457,823 A | 10/1995 | Mojena | |
| 6,151,972 A | 11/2000 | Venter et al. | |
| 6,299,606 B1 | 10/2001 | Young | |
| 6,338,166 B1 | 1/2002 | Hereford | |
| 6,428,521 B1 | 8/2002 | Droll | |
| 6,651,259 B1 * | 11/2003 | Hartman | A61B 10/007 4/144.1 |
| D488,226 S | 4/2004 | MacDonald et al. | |
| 6,775,852 B1 | 8/2004 | Alvarez et al. | |
| 6,811,754 B2 | 11/2004 | House | |
| D567,368 S | 4/2008 | Guptill | |
| 7,435,242 B2 | 10/2008 | Levinson | |

(Continued)

*Primary Examiner* — Jason K Niesz
(74) *Attorney, Agent, or Firm* — C. Brandon Browning; Maynard, Cooper & Gale, PC

(57) ABSTRACT

A single-use, biodegradable, paper urine collector and method of using same, the urine collector including a funnel body having a sloped continuous sidewall, a sloped base, a top opening, a funnel hole located at the lowest region of the sloped base and, optionally, a urine sample container operatively coupled to the sloped base. To convey funneled urine into the container, a top edge of the container is positioned within the funnel hole and the base of the container is positioned outside the funnel body. The funnel body is configured to funnel a stream of urine through the top opening and along an interior surface of the funnel body toward and through the funnel hole.

20 Claims, 10 Drawing Sheets

(56) References Cited

U.S. PATENT DOCUMENTS

| | | |
|---|---|---|
| D607,995 S | 1/2010 | Miller |
| 7,981,053 B2 | 7/2011 | Fleshman |
| 8,597,207 B1 | 12/2013 | Perry |
| D802,122 S | 11/2017 | Roudik |
| D804,654 S | 12/2017 | Stephen |
| 2002/0169395 A1 | 11/2002 | Huang |
| 2009/0209881 A1* | 8/2009 | Willcocks ............ A61B 10/007 600/573 |
| 2012/0210503 A1 | 8/2012 | Anzivino, Sr. et al. |
| 2014/0371628 A1 | 12/2014 | Desai |
| 2016/0089118 A1 | 3/2016 | Petersilia |
| 2017/0281399 A1 | 10/2017 | VanMiddendorp et al. |

* cited by examiner

BIODEGRADABLE URINE COLLECTOR

CROSS-REFERENCE TO RELATED APPLICATION

This application is a continuation-in-part of U.S. patent application Ser. No. 16/657,809, "Biodegradable Urine Collector", filed on Oct. 18, 2019, which claims priority to U.S. Provisional Patent Application No. 62/747,279, titled, "Biodegradable Female Urine Collector," filed on Oct. 18, 2018, the entire contents of which are incorporated herein by reference.

TECHNICAL FIELD

The present invention is directed to a urine collector and, more particularly, a biodegradable urine collector configured for more efficient collection of urine from a person without the person coming in contact with the urine during collection or urine sample handling.

BACKGROUND

It can be difficult to guide urine into a collection device and to avoid coming into contact with urine when providing a urine sample. Urine samples are collected frequently at places such as doctor's offices, laboratories, hospitals, retirement homes, nursing homes and other locations. Samples may need to be collected from both male and female individuals for a variety of purposes and often involve transport or handling after the sample has been provided.

Typically, a urine sample is collected using only a "hat" or cup. Sample providers may find it difficult to guide urine into a hat or cup, and to avoid coming into contact with urine while attempting to catch their urine sample when using only a hat or cup. For instance, the hat or cup can be misaligned with the urine stream and urine flow may not be directed into an opening of the hat or cup. Sometimes, not enough urine is collected. Sometimes, too much urine is provided or the urine in the hat or cup is disturbed and the hat or cup overflows or spills. Handling of such hat and cups can be inconsistent as well, especially if surfaces of the hat or cup become wet during the urine collection process. Others who retrieve urine samples for evaluation may also come into contact with urine that is on surfaces of the hat or cup containing the sample.

For female providers and minor children, in particular, providing and collecting a urine sample using only a hat or cup may pose a further increased likelihood that the provider will come into contact with urine during the sample collection process. Improved techniques for urine collection are generally desirable.

SUMMARY OF THE INVENTION

The present invention is directed to a urine collector and methods of using same. The urine collector allows for the collection of a stream of urine and direction of the urine into a container while avoiding contact of the provider with the urine stream during the collection. According to one aspect of the invention, there is provided a urine collector including a funnel body with a gripping area. The funnel body includes at least one side, a sloped base surrounded by and contiguous with a lower portion of the at least one side, a top opening bordered by a top perimeter of the at least one side, and a funnel hole located at a lowest region and/or center of the sloped base. In order to funnel a stream of urine from a subject using the funnel body, urine is directed through the top opening of the funnel body and along an interior surface of the funnel body toward and through the funnel hole when the funnel body is upright. Detachably connected to the funnel body is a container with at least one sidewall, a base surrounded by and contiguous with a lower portion of the at least one sidewall, and an open mouth bordered by a top edge of the at least one sidewall. In cross section, the open mouth of the container is essentially equal to a funnel hole cross section. With these similar cross section shapes, the funnel body is configured to receive and support the container and to convey funneled urine into the container when the top edge of the container is positioned within the funnel hole and the base of the container is positioned outside the funnel body. The urine collector is at least partially biodegradable and the container is removable from the funnel body without causing damage to the container or loss of container contents.

The funnel body may include four sides, the first and fourth sides being longer than the second and third sides. In these instances, the gripping area extends outward from a top portion of the first side, and a spout is formed from a top portion of the fourth side, so that the gripping area and the spout are located opposite each other about the funnel body. In other instances, funnel body is essentially hammock-shaped, and the at least one side is a sloped sidewall with a spout formed from a top portion of the sloped sidewall and located approximately opposite the gripping area about the funnel body. An exterior surface of the gripping area may include a plurality of gripping structures configured to enhance grip of the urine collector. These gripping structures may be ribs that extend essentially around the gripping area and are oriented so that a longitudinal axis of the gripping area is essentially orthogonal to a cross-section of the ribs. In some instances, the gripping area is a handle.

In one embodiment, the funnel hole is surrounded by a projection located on an exterior surface of the sloped base, the projection extending into the funnel hole and creating a smaller projection hole beneath the funnel hole. In this embodiment, because the projection hole cross section is smaller than the funnel hole cross section, the projection is configured to receive and support a rim extending outward from the top edge of the container and to position the container within the funnel hole.

In another embodiment, the mouth cross section and the funnel hole cross section are each in the shape of a circle. The funnel hole may be surrounded by a threaded sidewall that is complementary to a threaded portion of a top exterior surface of the container, such that the funnel body is configured to receive and support the container in the funnel hole when the container is screwed into the funnel hole.

According to yet another aspect of the invention, there is provided a method of collecting urine from a subject. The method includes first providing a urine collector with a funnel body and a container. The funnel body may be essentially hammock-shaped with a top opening bordered by a sloped sidewall and have a funnel hole located at a lowest region of a sloped base. The container may have at least one sidewall, a base surrounded by and contiguous with a lower portion of the at least one sidewall, and an open mouth bordered by a top edge of the at least one sidewall. The container is placed in the funnel hole of the funnel body, the cross section of the open mouth being essentially equal to a funnel hole cross section to allow for placement. During placement, the top edge of the container is positioned within the funnel hole and the base of the container is positioned outside the funnel body. A subject may then administer a stream of urine through the top opening, so that the urine is directed along an interior surface of the funnel body toward and through the funnel hole when the funnel body is upright. The urine is collected in the attached container. In some instances, the subject of urine collection is a female. The urine collector is at least partially biodegradable, and the container may be removed from the funnel body after urine has been collected within the container.

A further understanding of the nature and advantages of the present invention will be realized by reference to the remaining portions of the specification and the drawings.

BRIEF DESCRIPTION OF DRAWINGS

The urine collector and method of using same can be better understood, by way of example only, with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

The present invention is generally directed to a urine collector 10 and methods of using same for the collection of urine from a provider without exposing the provider to contact with the urine. In some instances, the provider is a female. Urine collector 10 includes a funnel body 12 for funneling urine into a detachable container 14. To avoid contact with urine during collection, funnel body 12 has a gripping area 16 for handling urine collector 10. In this way, urine collector 10 is positioned to collect a stream of urine from a provider while the hand of the provider avoids the urine stream. Funnel body 12 is sloped to convey urine to container 14, while providing an opening sufficiently large to accommodate and collect the stream of urine. As the collected urine is assisted into container 14 by funnel body 12, contact of urine with the exterior of container 14 is minimized or substantially eliminated. Thus, following the removal of container 14 from funnel body 12, container 14 with the collected urine may be handled without exposure of the handler to urine.

Figure 3:
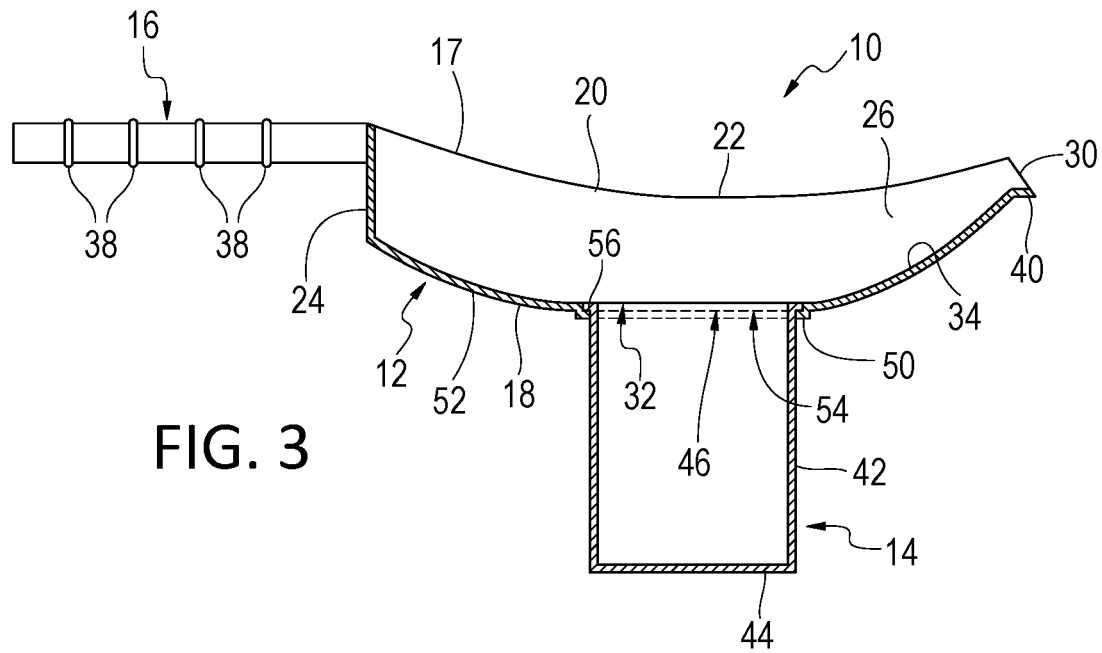
FIG. 3 is a sectional view of the urine collector of FIG. 1.
Figure 4:
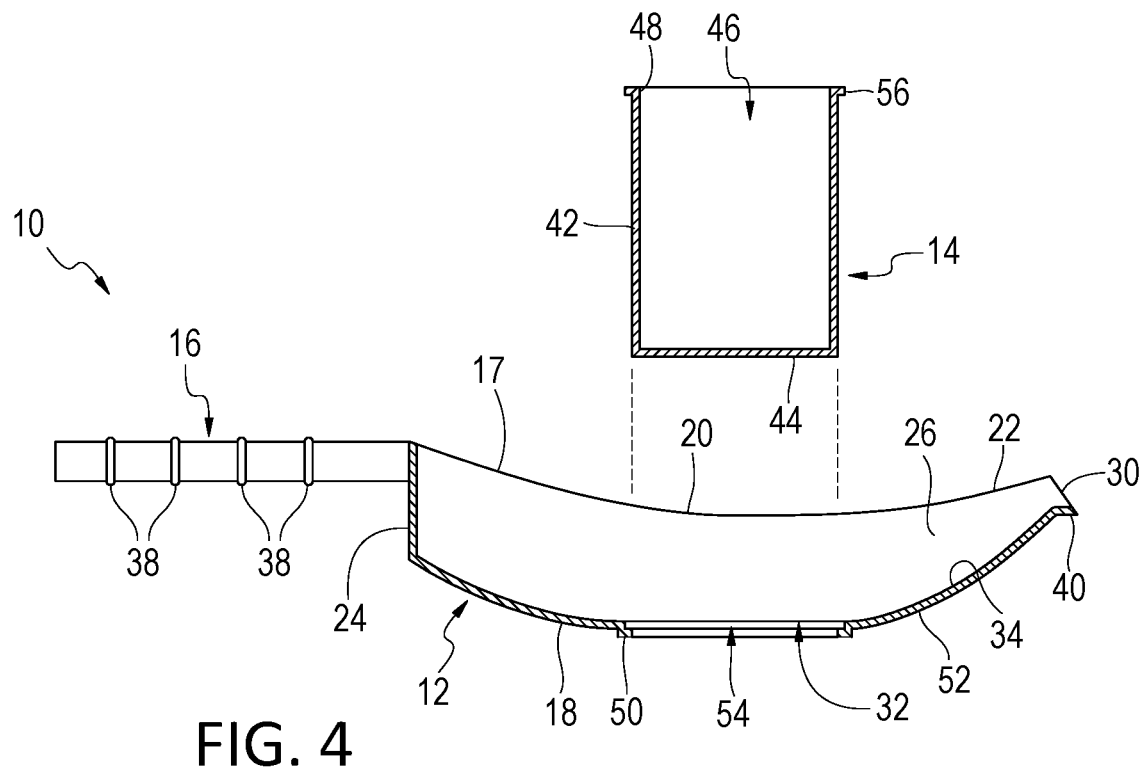
FIG. 4 is an exploded sectional view of the urine collector of FIG. 1 with the container separated therefrom.
Figure 5:
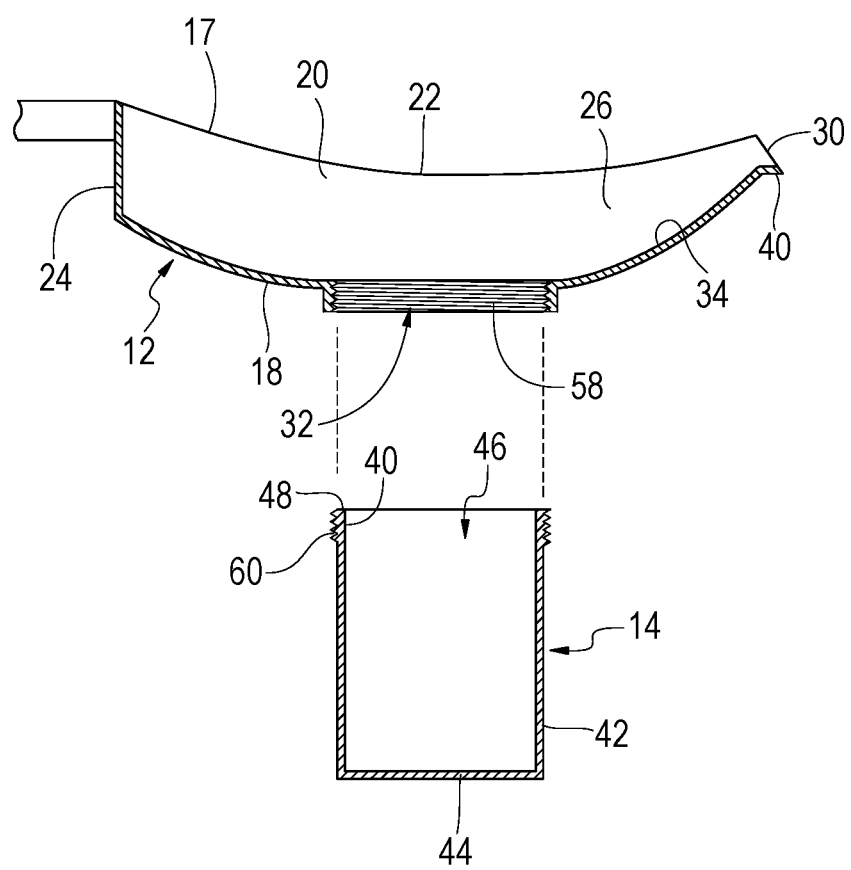
FIG. 5 is an exploded sectional view of a urine collector in accordance with a second embodiment of the present invention showing a container separated therefrom.
Figure 6:
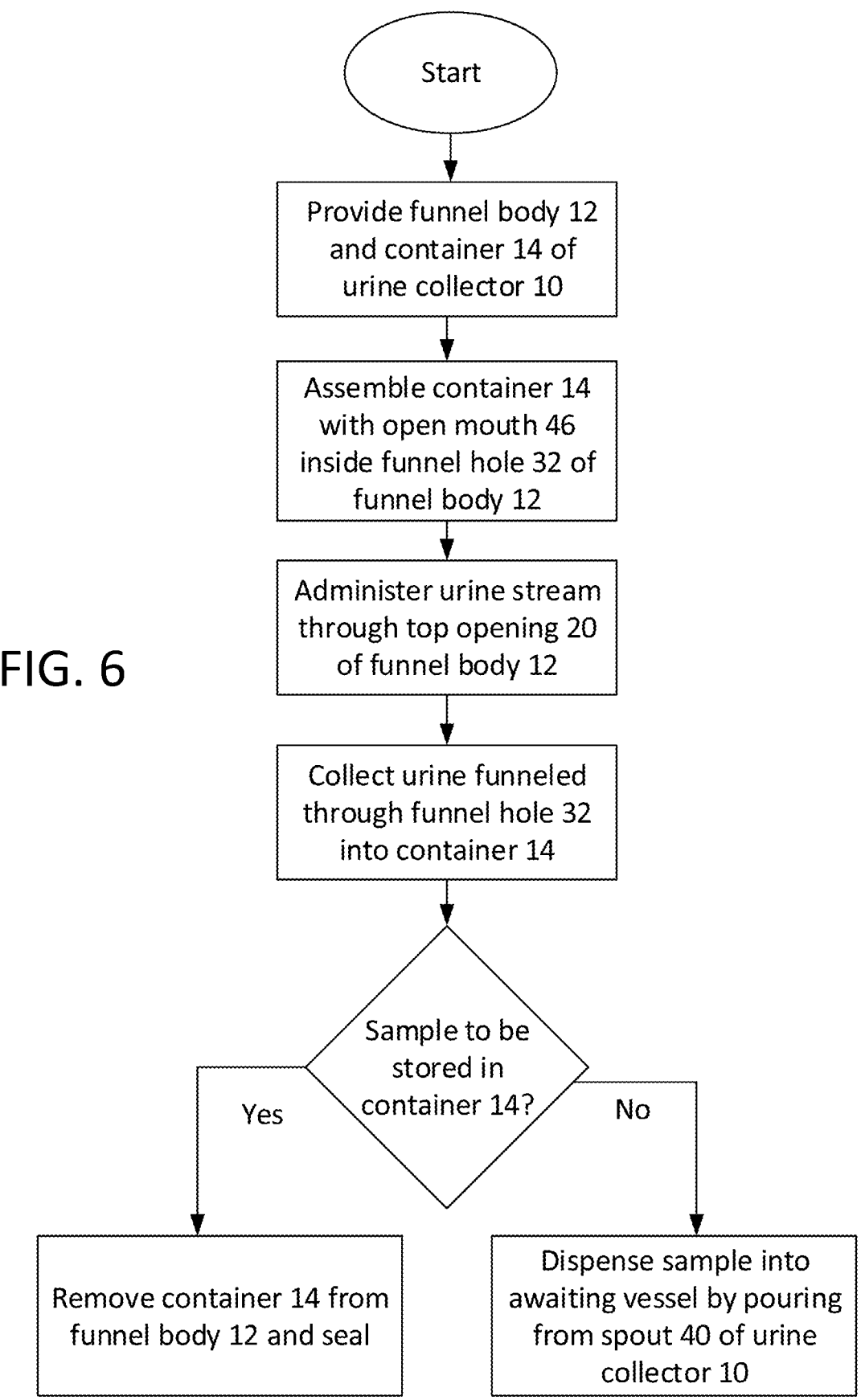
FIG. 6 is a flow chart describing the collection of urine using the urine collector of FIG. 1.
Figure 7:
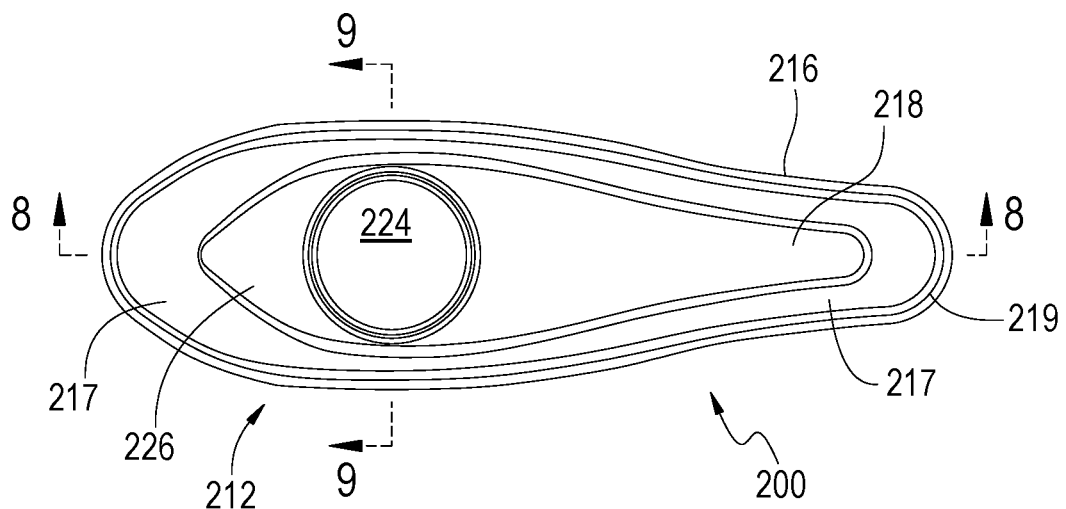
FIG. 7 is a plan view of a urine collector in accordance with a third embodiment of the preset invention.
Figure 8:
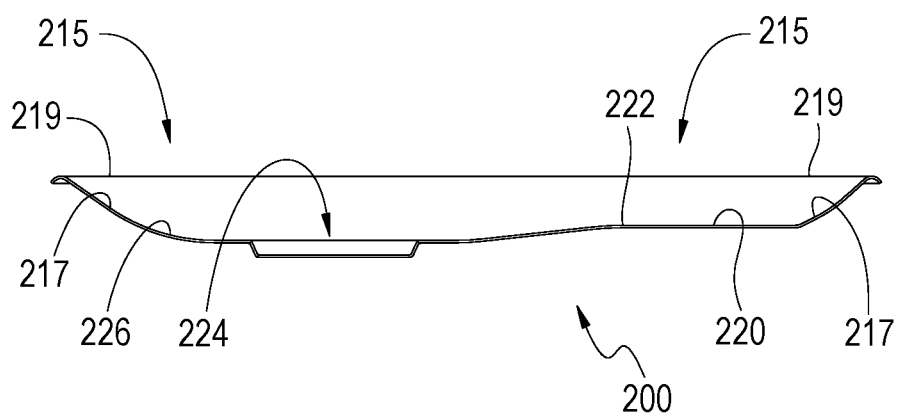
FIG. 8 is a sectional view of the urine collector of FIG. 7 along line A-A.
Figure 9:
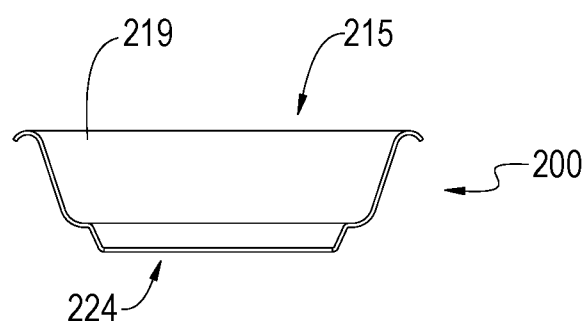
FIG. 9 is a sectional view of the urine collector of FIG. 7 along line B-B.
Figure 10:
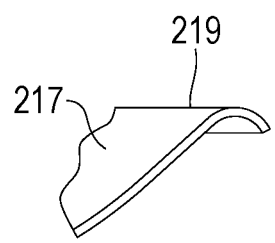
FIG. 10 is a detail view of the urine collector of FIG. 8 at C.

FIGS. 1 through 4 of the application depict urine collector 10 in accordance with a first embodiment of the present invention, and FIG. 5 depicts a urine collector 100 in accordance with a second embodiment of the present invention, where like features share like reference numerals. FIG. 6 of the application describes a method of using urine collector 10. FIGS. 7 through 10 of the application depict a urine collector 200 in accordance with a third embodiment of the present invention. FIGS. 11 through 17 of the application depict a urine collector 300 in accordance with a fourth embodiment of the present invention. It should be noted that all terms as used herein are given their common meaning as known in the art and as further described and discussed hereafter. As used herein, the singular forms "a", "an", and "the" include plural referents unless the context clearly indicates otherwise.

Figure 1:
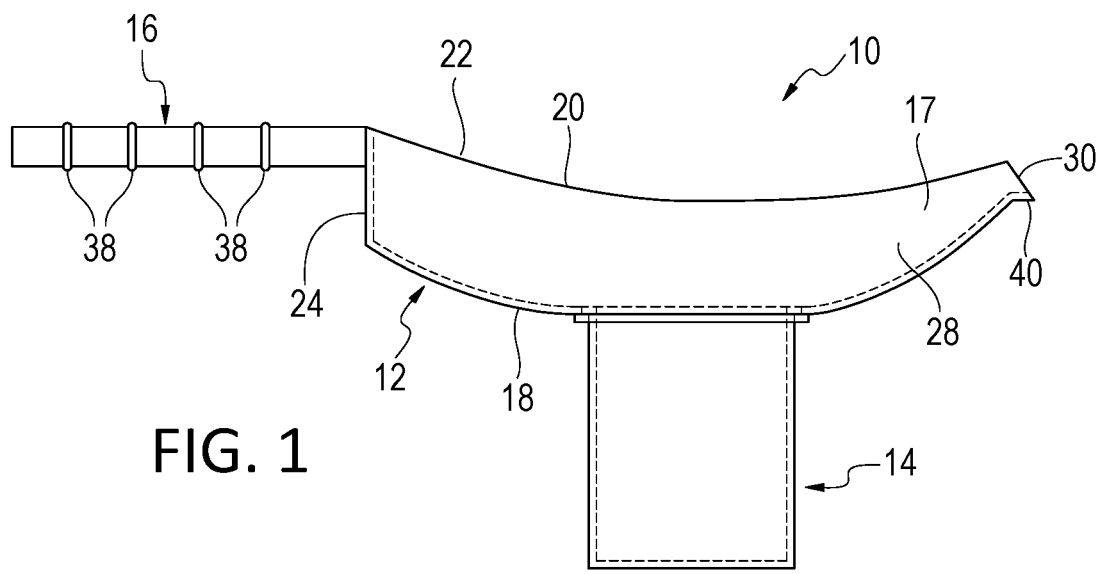
FIG. 1 is an elevational view of a urine collector in accordance with a first embodiment of the present invention including a detachable collection container.
Figure 2:
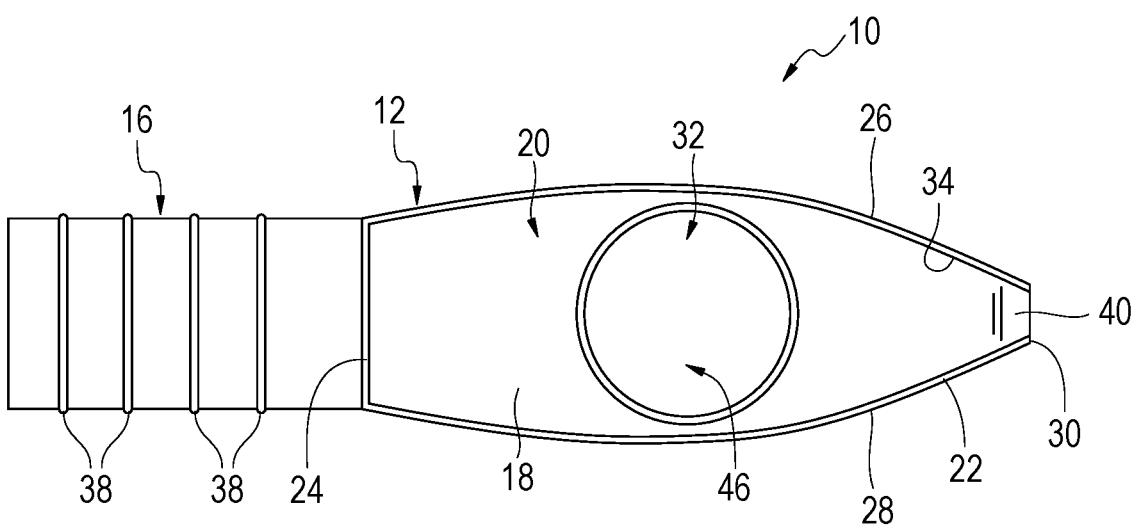
FIG. 2 is a plan view of the urine collector of FIG. 1.

In FIGS. 1 and 2, urine collector 10 is shown with container 14 inserted in funnel body 12. Urine collector 10 is at least partially biodegradable, and in some instances is entirely biodegradable. Exemplary biodegradable materials that may be used to construct collector 10 and/or container 14 include paper, paperboard, or other such environmentally-friendly materials. The at least partially biodegradable material of urine collector 10 makes up portions or the entirety of container 14, funnel body 12, or both container 14 and funnel body 12. In some embodiments, the entire urine collector 10 is fabricated from the same biodegradable material, but in other embodiments, a plurality of biodegradable materials are used. In one instance where the material is paperboard, the paperboard has exemplary properties such as a nominal base weight ranging from about 132 to about 280 lbs./3,000 Sq. Ft., and preferably about 185 lbs./3,000 Sq. Ft.; a caliper ranging from about 0.011 to about 0.024 inches, and preferably about 0.018 inches; a Taber stiffness in the machined direction ranging from about 80 to about 475 g-cm, and preferably about 230 to about 240 g-cm; a Taber stiffness in the cross direction ranging from about 30 to about 200 g-cm, and preferably about 95 g-cm; an elongation percentage in the machined direction ranging from about 2.3% to about 2.6%, and preferably about 2.6%; an elongation percentage in the cross direction ranging from about 4.4% to about 5.8%, and preferably about 5.8%; and a moisture percentage ranging from about 6.8% to about 7.5%, and preferably about 7.5%. In some instances, the paperboard is uncoated, and in other instances, the paperboard is coated by a polymer film. In one embodiment, the paperboard is coated on a single side or on both sides by a polyethylene film (PET). The PET film has exemplary properties such as a thickness ranging from about 0.5 to about 1 millimeters, a weight ranging from about 7.2 to about 14.4 lbs./3,000 Sq. Ft., and a transparency ranging from opaque to transparent. In one instance, the paperboard is laminated with 48 Gauge PET. The thickness, density, color, or other properties of the collector material may be varied as suitable to achieve desired properties of urine collector 10. In certain instances, the collector is fabricated from a single sheet of paper or paperboard.

FIG. 1 displays urine collector 10 with funnel body 12 configured to channel fluid that enters funnel body 12 into container 14. Urine collector 10 has an overall length of approximately 1 foot and 13/16 inches, but other dimensions are possible. Funnel body 12 has an essentially hammock or banana-shaped profile when viewed from a side as shown in FIG. 1, or an essentially tear-drop shaped profile when viewed from above, such as in FIG. 2, or may have various other shapes suitable to capture a stream of urine from a subject and convey the urine to container 14. Additionally, funnel body 12 has a width of approximately 2⅝ inches, a length of approximately 8 5/16 inches, and a height of approximately 2 7/16 inches, though other dimensions are possible. Funnel body 12 is configured to channel any liquid inside to container 14 using sloped sidewalls or at least one side 17, including an embodiment where funnel body 12 has four sides. A sloped base 18 is surrounded by and contiguous with a lower portion of sloped sidewalls or at least one side 17, where sloped base 18 has a lowest region in which funneled liquid is directed. Funnel body 12 further includes a top opening 20 bordered by a top perimeter 22 of sloped sidewalls or at least one side 17, which is described below in detail.

In the embodiment where funnel body 12 has four sides, a first side 24 and a fourth side 30 are located approximately opposite each other about funnel body 12. Similarly a second side 26 and a third side 28 are located approximately opposite each other about funnel body 12. The at least one side or sloped sidewalls 17 may be curved or straight in profile, as shown in FIG. 2. The lengths of first and fourth sides 24, 30 are less than the lengths of second and third sides 26, 28. In some instances, second and third sides 26, 28 are equal in shape, length, width, and height and in other instances the shape, length, width, and height of second and third sides 26, 28 differ. For example, second and third sides 26, 28 each have a height of approximately 2 7/16 inches, though other dimensions are possible. In some instances, first and fourth sides 24, 30 are equal in shape, length, width, and height and in other instances, first side 24 is larger than and has a different shape from fourth side 30. Connections between sloped sidewalls or at least one side 17 may be rounded or result in corners at intersections. Similarly, connections between sloped sidewalls or at least one side 17 and sloped base 18 may be rounded or result in corners at intersections.

As shown in FIG. 2, funnel body 12 includes top opening 20 capable of receiving a stream of urine. Top opening 20 is sufficiently large such that a stream of urine is collected within funnel body 12 with reduced or substantially no flow of urine outside urine collector 10. Funnel body 12 is configured to channel fluid that enters through top opening 20 toward a funnel hole 32 located at the lowest region of sloped base 18. Urine that enters through top opening 20 is directed along an interior surface 34 of funnel body 12, including sloped sidewalls or at least one side 17 and sloped base 18, toward and through funnel hole 32 when funnel body 12 is upright. Funnel hole 32 is shaped as a circle, rounded quadrilateral, oval, quadrilateral, or any other shape suitable for directing liquid into a similarly-shaped container mouth. In the instance where funnel hole 32 is shaped as a circle, it has an approximately 2½ inch diameter, though other dimensions are possible.

FIGS. 1 through 5 display the gripping area 16 extending from an upper exterior surface of sloped sidewalls or at least one side 17 of funnel body 12. In the instance where funnel body 12 has four sides, gripping area 16 extends outward from a top portion of first side 24. Gripping area 16 is approximately parallel to a cross section of funnel hole 32 in some embodiments, and may be sloped relative to the cross section of funnel hole 32 in other embodiments. Gripping area 16 has a width of approximately 2½ inches, a length of approximately 4½ inches, and a thickness of approximately ½ inch, though other dimensions are possible. In some instances, gripping area 16 is made from one material, and in other instances, gripping area 16 includes at least two materials. A subject may use gripping area 16 to position funnel body 12 for receiving urine from the subject's urine stream, such as positioning funnel body 12 beneath the subject's trunk and between the subject's legs.

In some embodiments, gripping area 16 is a handle. Gripping area 16 may have essentially flat surfaces, or it may have contours or other features as desired to improve a subject's ability to hold gripping area 16 securely while using urine collector 10. In some instances, gripping area 16 includes a plurality of gripping structures 38 on its surface for enhancing grip while a subject is holding urine collector 10. Gripping structures 38 include raised textures such as circles, grid patterns, ribs, or other suitable structures or patterns for enhancing grip. In some instances, gripping structures 38 are formed of the same material as gripping area 16 as a unitary construction or as separate components attached to gripping area 16. In other instances, gripping structures 38 are coated on the surface of gripping area 16 using a material that is different from the material of gripping area 16. In the embodiment depicted in FIGS. 1 through 4, gripping structures 38 are a plurality of ribs extending essentially around gripping area 16 and oriented so that a longitudinal axis of gripping area 16 is essentially orthogonal to a cross section of gripping structures 38. However, gripping structures 38 may be oriented and positioned in other suitable configurations about gripping area 16 such that grip is enhanced. Gripping structures 38 are spaced about 1 inch apart from each other in the depicted embodiment, but other separations are possible. Spacing of gripping structures 38 is equal in some instances and unequal in other instances. Gripping structures 38 are positioned in at least one group or cluster on the surface of gripping area 16 in some embodiments. The ribs or gripping structures 38 of FIGS. 1 through 4 have a thickness of approximately ⅛ of an inch, but other dimensions are possible. In addition, although approximately four gripping structures 38 are shown in FIGS. 1 through 4, various other quantities of ribs or gripping structures 38 are possible in other embodiments.

Referring to embodiments depicted in FIGS. 1 through 5, funnel body 12 further includes a spout 40 configured to direct urine from within urine collector 10 over a surface of spout 40 and out of urine collector 10, such as when funnel body 12 is tilted sufficiently to pour the urine out. Poured urine may be disposed of in this manner, or may be poured into a receiving vessel for further storage or handling. Spout 40 may have various shapes suitable for pouring liquid without spilling the liquid from the sides of spout 40 or funnel body 12. The location of spout 40 is near a top portion of at least one side or sloped sidewall 17. In the embodiments shown in FIGS. 1 through 5, spout 40 is located opposite gripping area 16 about funnel body 12, though other sloped sidewall 17 locations of spout 40 are possible. In instances where funnel body 12 has four sides, gripping area 16 is located on first side 24 and spout 40 is located on fourth side 30. Spout 40 is approximately ½ of an inch wide and approximately ½ of an inch tall in the depicted embodiments, though other dimensions are possible. Spout 40 can have a trough, channel or other features to achieve the functionality described herein.

As shown in FIGS. 1 through 4, container 14 is received in funnel hole 32 for the collection of funneled urine. Container 14 includes at least one sidewall 42, a lower portion of which surrounds and is contiguous with a base 44. An open mouth 46 of container 14 is opposite base 44 and is formed by a top edge 48 of at least one sidewall 42. Container 14 is made of the same material as funnel body 12 in some instances, or differs in composition in other instances. For example, container 14 may be made of paper, paperboard, or other recyclable or environmentally-friendly materials, as well as materials such as plastic. The shape of base 44 is the same shape as the cross section of funnel hole 32 in some instances and differs from that of funnel hole 32 in other instances. At least one sidewall 42 completely surrounds base 44 and may be of unitary construction with base 44 or comprise separate components that are attached to form container 14. One or more sidewalls are contemplated for making up at least one sidewall 42.

Open mouth 46 and funnel hole 32 are of a similar shape and size, such that the dimensions of top edge 48 are equal to or slightly larger than the dimensions of the cross section of funnel hole 32. Thus, container 14 is placed in funnel hole 32 either through top opening 20 or from below funnel body 12, such that open mouth 46 is positioned within funnel hole 32 and base 44 of container 14 extends outside funnel body 12. In this position, open mouth 46 of container 14 is configured to receive urine provided by funnel body 12 through funnel hole 32. Urine from a stream entering through top opening 20 of funnel body 12 is thus channeled toward funnel hole 32 and into container 14 when container 14 is positioned within funnel hole 32.

Referring to the embodiment depicted in FIGS. 1 through 4, funnel body 12 further includes an annular projection 50 for positioning and securing container 14 within funnel hole 32. Projection 50 is located on an exterior surface 52 of funnel body 12, bordering funnel hole 32. Further, projection 50 extends within the cross section of funnel hole 32 to form a projection hole 54 that is the same shape but smaller in dimensions than funnel hole 32. As shown in FIGS. 3 through 4, when container 14 is inserted into funnel hole 32, a rim 56 on an exterior top surface of at least one sidewall 42 of container 14 sits upon projection 50. This positioning, as shown in FIG. 3, allows top edge 48 of container 14 to be approximately flush with interior surface 34 of funnel body 12 and for urine that channels along interior surface 34 to exit funnel hole 32 and enter container 14 through open mouth 46. Projection 50 extends a distance into funnel hole 32 approximately equal to the thickness of rim 56, so that container 14 fits within funnel hole 32 without substantial space between rim 56 and borders of funnel hole 32 and so that rim 56 does not sit on interior surface 34 of sloped base 18 and extend into funnel body 12. In this embodiment, container 14 is inserted through top opening 20 and into funnel hole 32, as shown in FIG. 4, though insertion of container 14 through an underside of funnel hole 32 is possible when projection 50, rim 56, or both are flexible structures that can be temporarily deformed during insertion. Container 14 is configured for removal from funnel body 12 by pushing and/or lifting container 14 out of funnel hole 32 and through top opening 20. Alternatively, funnel body 12 may be pulled off of container 14 for removal in instances where projection 50, rim 56, or both are flexible structures. Container 14 may be capped or sealed for further handling of contained urine.

In another embodiment shown in FIG. 5, funnel body 12 of urine collector 100 includes a threaded sidewall 58 for positioning and securing container 14 within funnel hole 32. Threaded sidewall 58 is a wall that borders funnel hole 32 and is complementary to a threaded portion 60 of a top exterior surface of container 14. Thus, threaded portion 60 allows container 14 to be screwed into threaded sidewall 58 of funnel hole 32, positioning and securing container 14 in funnel hole 32. In this position, top edge 48 of container 14 is approximately flush with interior surface 34 of funnel body 12, so that urine channeled along interior surface 34 exits funnel body 12 through funnel hole 32 and enters container 14 through open mouth 46. Container 14 is inserted from below funnel body 12 in some instances, by first aligning open mouth 46 with funnel hole 32 and then holding and rotating at least one sidewall 42 while funnel body 12 is held stationary or counter-rotated. In other instances, container 14 is inserted through top opening 20 and into funnel hole 32 by first aligning open mouth 46 with funnel hole 32 and then holding and rotating at least one sidewall 42 while funnel body 12 is held stationary or counter-rotated. In either instance where threaded container 14 is inserted, container 14 may be held stationary while funnel body 12 is rotated for insertion. The threads of threaded sidewall 58 are complementary to those of threaded portion 60 for a secure gripping of container 14 within funnel hole 32 and to facilitate screwing and unscrewing of container 14. Moreover, container 14 is configured for removal from funnel body 12 by unscrewing threaded portion 60 and threaded sidewall 58 in the same positions discussed for insertion, but by rotating in an opposite direction. After removal, container 14 may be capped with a cap that screws onto threaded portion 60 to secure contained urine during handling.

Referring to FIGS. 7 through 10, there is depicted a urine collector 200 in accordance with a third embodiment of the present invention. Urine collector 200 includes a funnel body 212 for funneling urine into a detachable container (not shown) and a gripping area 216 for handling urine collector 200. Funnel body 212 is sloped to convey urine to the container, while providing an opening sufficiently large to accommodate and collect the stream of urine.

Like urine collectors 10 and 100, urine collector 200 is constructed from biodegradable materials such as paper and paperboard and may be formed from a single-sheet of paper or paperboard. Urine collector 200 differs from collectors 10 and 100 in that collector 200 is shallower and provides a larger top opening 215 for collecting a stream of urine, which is accomplished in part by a sloped, continuous sidewall 217 that extends across funnel body 212 and into gripping area 216. Top opening 215 is bordered by a top perimeter 219 of sidewall 217 providing the top opening with a length of 12%₃₂ inches+/−³⁄₃₂ inches. Within gripping area 216, sidewall 217 is arranged to funnel or direct urine onto a gripping area floor 218 having a flat portion 220 and a downward sloped portion 222 arranged for directing urine collected in the gripping area to a funnel hole 224. Urine collector 200 has an overall length of 12⁴¹⁄₆₄ inches+/−³⁄₃₂ inches, but other dimensions are possible. Additionally, funnel body 12 has a width of approximately 4 inches+/−³⁄₃₂ inches and a height of approximately 1¹⁄₆₄ inches, though other dimensions are possible.

Funnel body 212 is configured to channel fluid that enters through top opening 215 toward a funnel hole 224 located at the lowest region of a sloped base 226. Urine that enters through top opening 215 is directed along an interior surface of funnel body 212 and/or gripping are 216 along sidewall 217 and sloped base 226, toward and through funnel hole 224 when funnel body s12 is upright. In the instance where funnel hole 32 is shaped as a circle, it has an approximately 2⅝ inch diameter, though other dimensions are possible.

A container (not shown) may be received in funnel hole 224 for the collection of funneled urine. Funnel hole 224 of urine collector 200 may include the funnel hole configuration of urine collector 10, i.e., where the container is lowered into the funnel hole, or the funnel hole configuration of urine collector 100, i.e., where the funnel hole is threaded Now referring to FIG. 6, a method for collecting urine from a stream of urine in urine collector 10 or 200 is described. Container 14 is first assembled in funnel hole 32 of funnel body 12 to form urine collector 10 or 200, forming a relatively uninterrupted, smooth path along interior surface 34 for urine to channel towards funnel hole 32. Urine collector 10 or 200 is then positioned beneath the torso and between the legs of a subject for the collection of the urine from the subject's urine stream. In some instances, the subject is a human female. The subject administers the urine stream through top opening 20 of funnel body 12, so that essentially the entire urine stream is directed into funnel body 12. Urine from the urine stream funnels along interior surface 34 toward and through funnel hole 32 and into attached container 14. In instances where urine is to be handled or stored in container 14, container 14 is removed from funnel body 12 with minimal or no spilling of urine and container 14 is optionally sealed for further transport or handling. In other instances where urine is not to be ultimately stored in container 14, urine is dispensed from urine collector 10 into an awaiting vessel using spout 40 to transfer the urine without substantial loss of urine or contact of the handler with the urine. Following a single use of collector 10 or 200, i.e., depositing a single sample of urine directly from a provider into the collector, collector 10 or 200 may be discarded. In other instances, collector 10 or 200 may be cleaned after use and then used with one or more subsequent urine samples.

Figure 11:
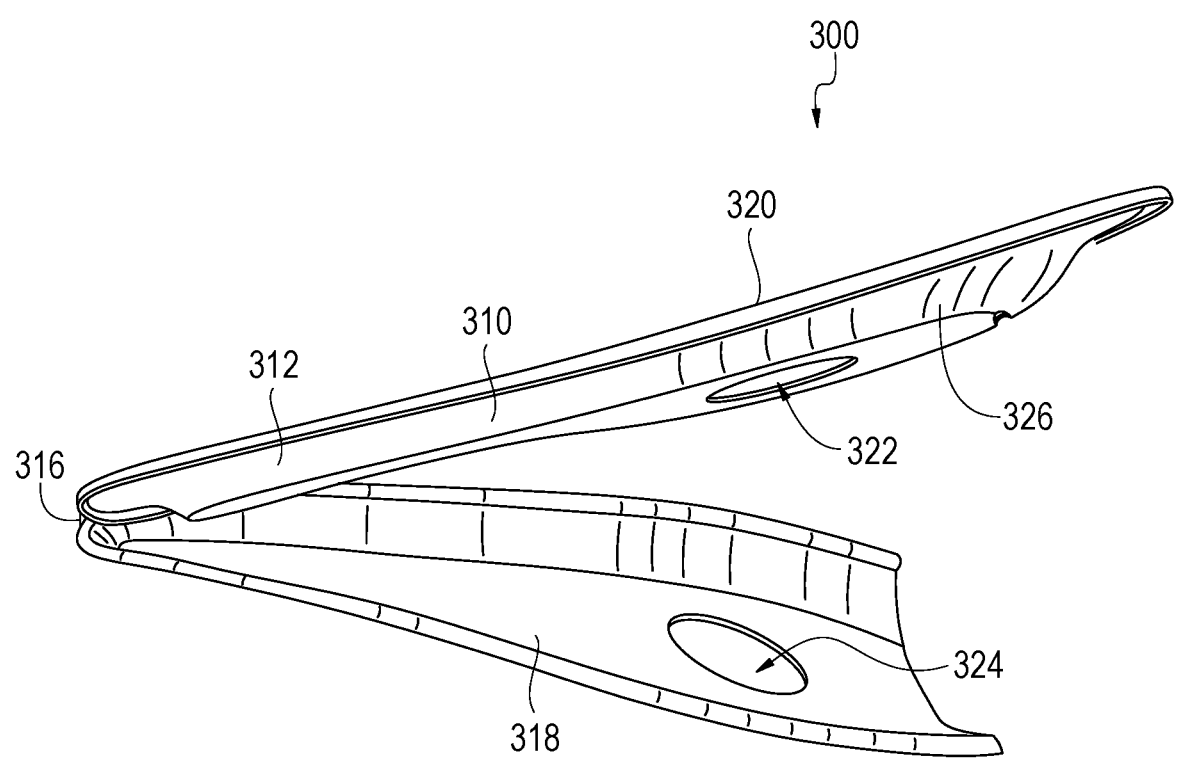
FIG. 11 is a perspective view of a side of a urine collector in accordance with a fourth embodiment of the present invention in an opened configuration.
Figure 12:
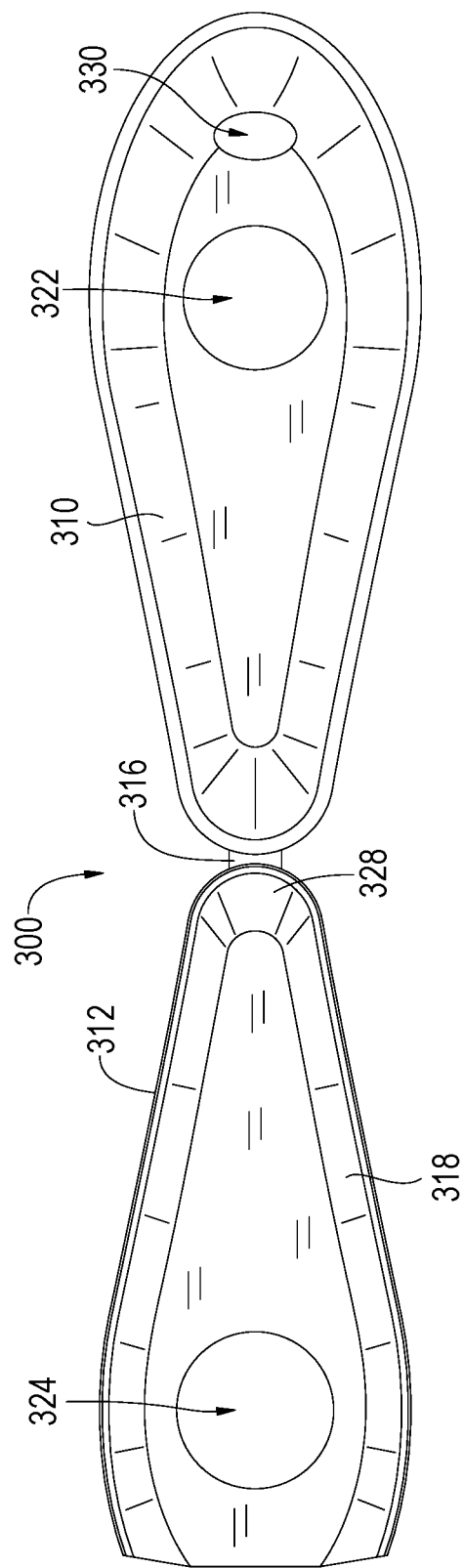
FIG. 12 depicts the urine collector of FIG. 11 in an open configuration showing a top of the top funnel and a bottom of the bottom funnel.
Figure 13:
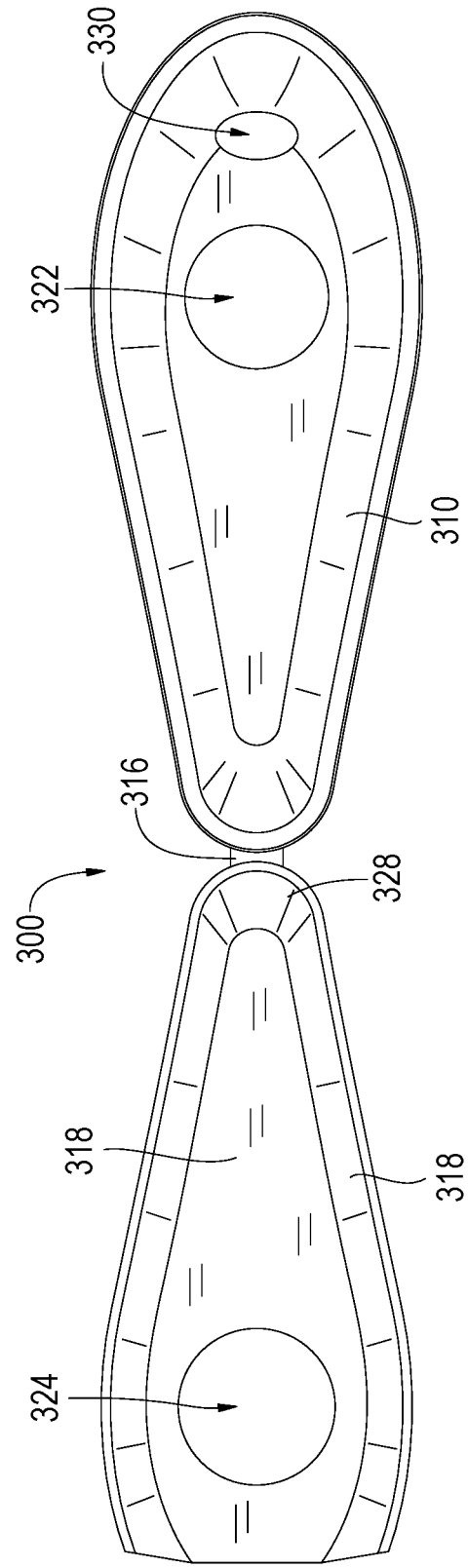
FIG. 13 depicts the urine collector of FIG. 11 in an open configuration showing a bottom of the top funnel and a top of the bottom funnel.
Figure 14:
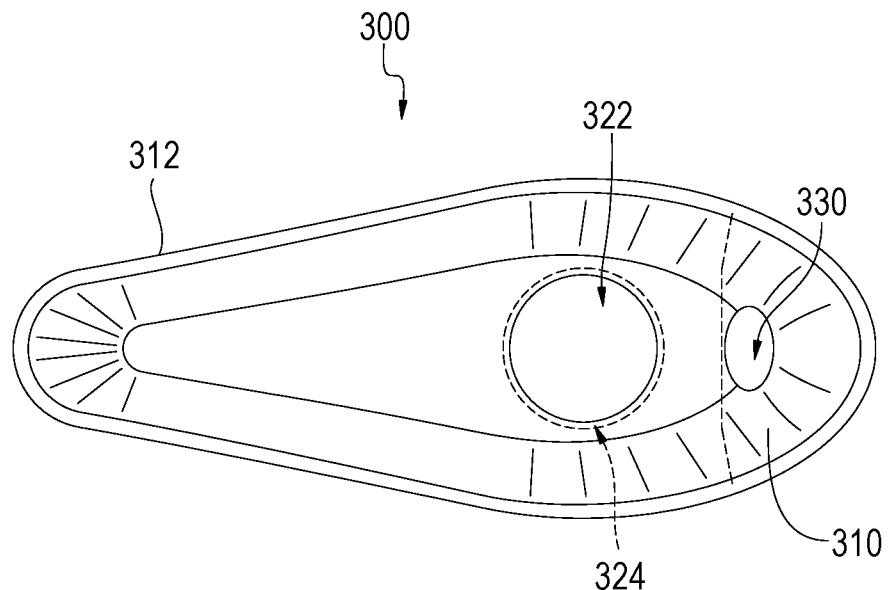
FIG. 14 depicts a top of the urine collector of FIG. 11 in a closed configuration.
Figure 15:
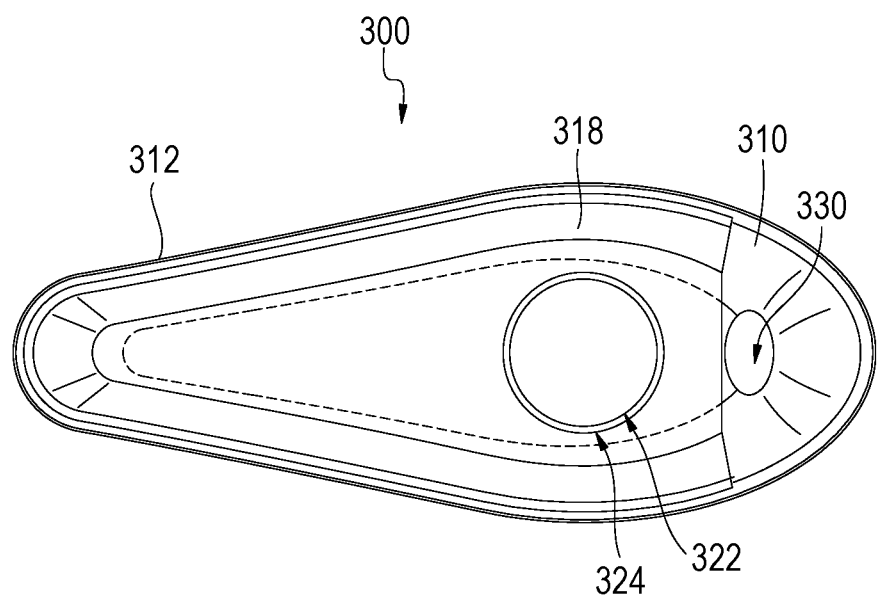
FIG. 15 depicts a bottom of the urine collector of FIG. 11 in a closed configuration.

Referring to FIGS. 11 through 17, there is depicted a urine collector 300 in accordance with a fourth embodiment of the present invention. The urine funneling capabilities of urine collector 300 are similar to those of embodiments described above. However, urine collector 300 includes several features that differ and are described in greater detail below. Urine collector 300 includes a funnel body 312 with an upper funnel 310 and a lower funnel 318 connected by a hinge 316, all of which are constructed of a single, continuous piece of material. The function of upper funnel 310 is to provide a collection site and pathway for urine to enter an upper funnel hole 322, while the function of lower funnel 318 is to hold a container 314 in position for urine to enter therein. Referring to FIG. 11, urine collector 300 is shown with no container inserted in its funnel body 312, and with funnel body 312 in an open configuration configured to receive container 314. FIG. 12 displays urine collector 300 with funnel body 312 in an open configuration from a top view of upper funnel 310, while FIG. 13 displays urine collector 300 with funnel body 312 in an open configuration from a bottom view of upper funnel 310. FIG. 14 shows a top view of urine collector 300 in the closed configuration, while FIG. 15 shows a bottom view of urine collector 300 in the closed configuration.

As shown in FIG. 11, upper funnel 310 is configured to channel fluid that enters through a top opening 320 toward upper funnel hole 322 located at the lowest region of a sloped base 326. Upper funnel hole 322 is shaped as a circle, rounded quadrilateral, oval, quadrilateral, or any other shape suitable for directing liquid into a similarly-shaped container mouth. Upper funnel hole 322 is smaller in diameter or other dimensions than a lower funnel hole 324 of lower funnel 318, such that urine does not leak or otherwise become directed outside lower funnel hole 324 after it enters upper funnel hole 322. As shown in FIGS. 12 through 15, funnel body 312 further includes a drain 330 to provide a path through which excess urine may flow when urine is directed into upper funnel 310. As such, urine that is not collected into container 314 through upper funnel hole 322 is instead directed into drain 330 and to a toilet or other waste receptacle beneath urine collector 300. Drain 330 allows urine to be collected without pooling in upper funnel 310. The dimensions of drain 330 vary based on urine collector size, and are such that drain 330 sufficiently removes excess pooling urine. The shape of drain 330 is depicted as an oval, though other shapes are compatible with the present disclosure. Drain 330 is located opposite hinge 316. Hinge 16 is shown to connect upper funnel 310 and lower funnel 318 at a location on a side 328 of each of upper and lower funnels 310, 318. Hinge 316 is shown to be of unitary construction with funnel body 312, though in embodiments not depicted it is a separate feature that is fixed onto side 328 of each of upper and lower funnels 310, 318. Hinge 316 is configured to open and close urine collector in a reversible manner, such that container 314 may be inserted or removed while funnel body 312 is in the open configuration and container 314 is maintained in position when funnel body 312 is in the closed configuration. A subject may grip near or on hinge 316 to position funnel body 312 for receiving urine from the subject's urine stream, such as positioning funnel body 312 beneath the subject's trunk and between the subject's legs.

FIG. 15 depicts a lower funnel hole 324 in lower funnel 318, which is approximately concentric with upper funnel hole 322. Similar to upper funnel hole 322, lower funnel hole 324 is shaped as a circle, rounded quadrilateral, oval, quadrilateral, or any other shape suitable for directing liquid into a similarly-shaped container mouth. The perimeter of lower funnel hole 324 contains small cuts or folds configured to expand the perimeter of lower funnel hole 324 to accommodate various sizes of containers 314. Thus, lower funnel hole 324 is configured to hold container 314, while upper funnel 310 is closed over lower funnel 318. When container 314 is located in lower funnel hole 324, urine directed through upper funnel hole 322 is similarly directed through lower funnel hole 324 and into the waiting container 314.

Figure 16:
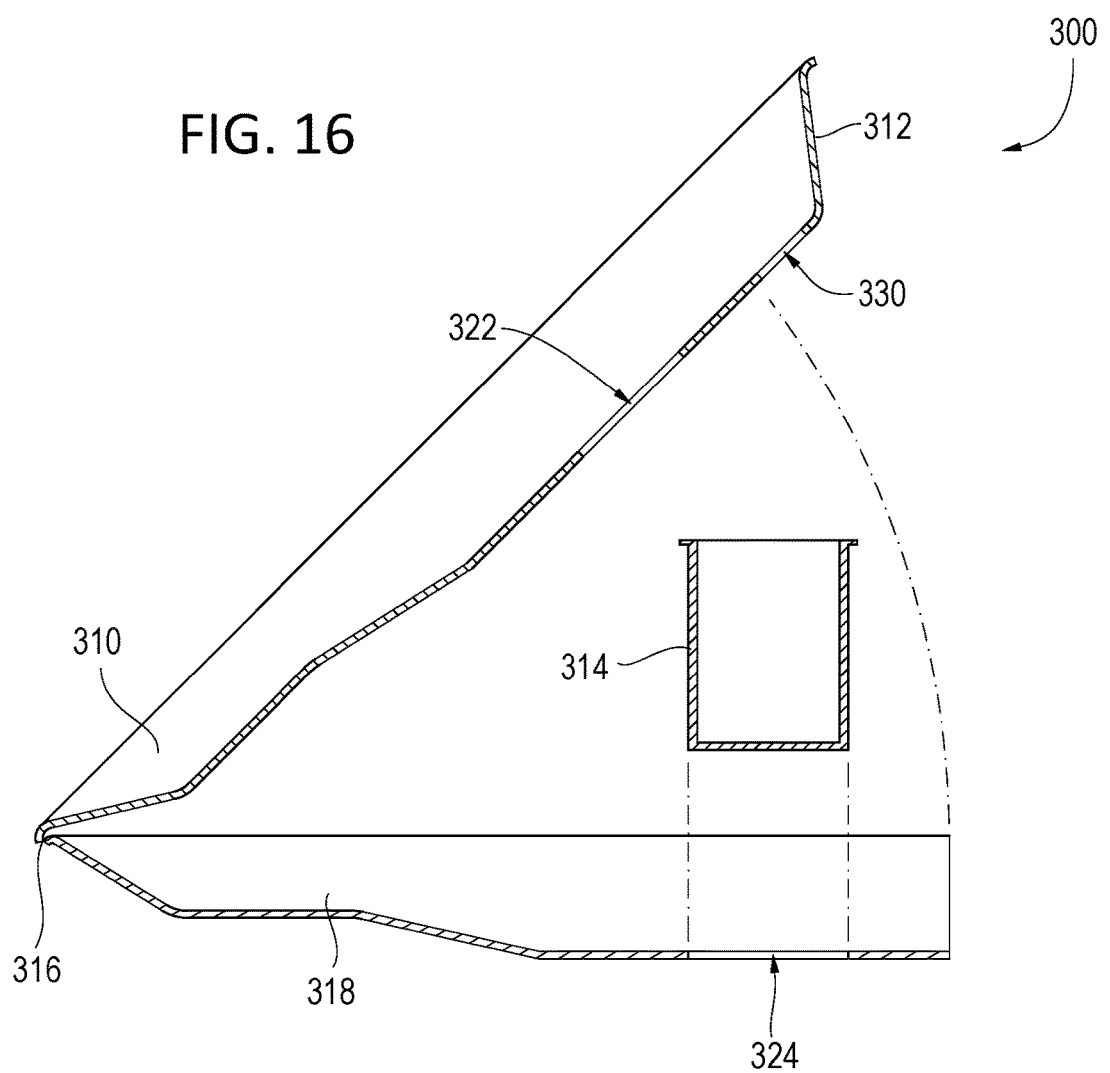
FIG. 16 is an exploded sectional view of the urine collector of FIG. 11 in an opened configuration with a collection container separated therefrom.
Figure 17:
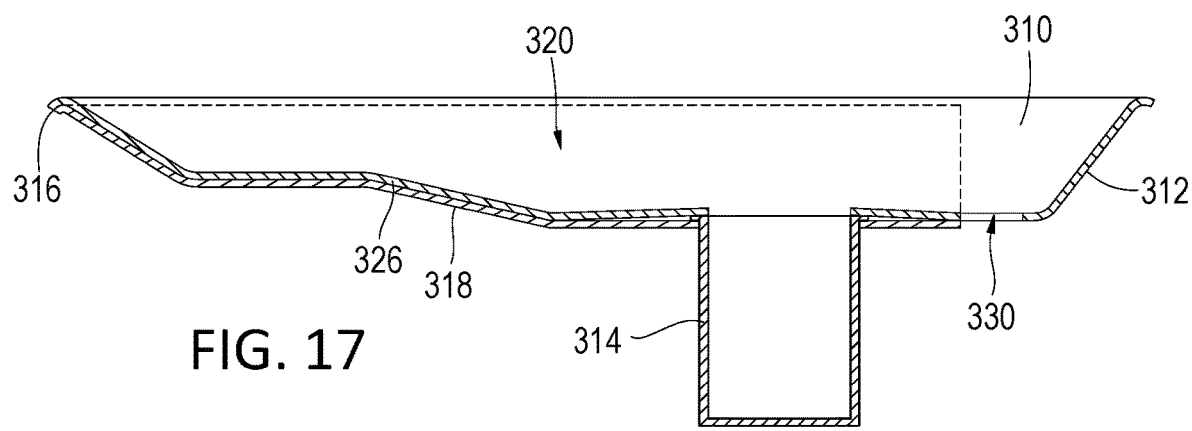
FIG. 17 is a sectional view of the urine collector of FIG. 11 in a closed configuration including the detachable collection container.

As shown in FIG. 16, container 314 is received in lower funnel hole 324 for the collection of funneled urine. Container 314 is placed in lower funnel hole 324 either through top opening 320 or from below funnel body 312, such that container 314 is configured to receive urine provided by funnel body 312 through upper and lower funnel holes 322, 324. Urine from a stream entering through top opening 320 of funnel body 312 is thus channeled toward upper and lower funnel holes 322, 324 and into container 314 when container 314 is positioned within lower funnel hole 324. When container 314 is inserted into lower funnel hole 324, a rim of container 314 rests just outside lower funnel hole 324. This positioning, as shown in FIG. 17, allows the rim of container 314 to be approximately flush with funnel body 312 and for urine to exit funnel holes 322, 324 and enter container 314. Thus, a user prepares urine collector 300 by first opening upper funnel 310, inserting container 314 into lower funnel hole 324, and closing upper funnel 310 over lower funnel 318. At this point, container 314 is positioned for the capture of urine. The user then places urine collector 300 in a position to capture a stream of urine from the user while holding urine collector 300 at or near hinge 316. When urine collection in container 314 is complete, container 314 is configured to be removed by lifting container 314 out of lower funnel hole 324 when urine collector 300 is in an open configuration. Container 314 with urine contents may then be sealed with a lid, cap, or other sealing means and stored or transported.

As will be understood by those familiar with the art, the present invention may be embodied in other specific forms without departing from the spirit or essential characteristics thereof. For example, the present invention may be utilized for the collection of other fluids, such as saliva, by orienting urine collector 10 as appropriate for the collection of such other fluids. Accordingly, the disclosures and descriptions herein are intended to be illustrative, but not limiting, of the scope of the invention which is set forth in the following claims.

What is claimed is:

1. A urine collector comprising:
  a funnel body including an upper funnel body with a gripping area and a first funnel hole, and a lower funnel body hingedly coupled to the upper funnel body, the lower funnel body including a gripping area and a second funnel hole,
  wherein the funnel body is selectively convertible between an open configuration adapted and arranged for loading a cup into the second funnel hole and a closed configuration adapted and arranged for aligning the first funnel hole with the second funnel hole and a mouth of the cup.

2. The urine collector of claim 1, wherein the upper funnel body includes a side, a sloped base surrounded by and contiguous with a lower portion of the side, and a top opening bordered by a top perimeter of the side, the first funnel hole being located at a lowest region of the sloped base,
  wherein the upper funnel body is configured to receive a stream of urine from a subject through the top opening of the upper funnel body, funnel the stream of urine along an interior surface of the upper funnel body toward and through the first funnel hole and the second funnel hole.

3. The urine collector of claim 1, wherein the funnel body is constructed entirely of paper.

4. The urine collector of claim 1, wherein the funnel body is constructed entirely from a single sheet of paper.

5. The urine collector of claim 1, wherein the first funnel hole has a dimeter that is less than the second funnel hole.

6. The urine collector of claim 1, wherein the funnel body is essentially hammock-shaped.

7. The urine collector of claim 1, wherein the upper funnel body includes a drain hole with a continuous sidewall.

8. A method of collecting urine using the urine collector of claim 1 comprising, while the funnel body is in the open configuration, loading the cup into the second funnel hole, followed by converting the funnel body into the closed configuration whereby the first funnel hole is aligned with the second funnel hole and the mouth of the cup, followed by directing urine into the upper funnel body, through the first funnel hole, the second funnel hole and the mouth and into the cup, followed by converting the funnel body into the open configuration, followed by removing the cup from the second funnel hole.

9. The urine collector of claim 1, wherein the second funnel hole diameter is expandable.

10. The urine collector of claim 9, wherein the second funnel hole diameter includes a plurality of cuts extending radially outward from the second funnel hole.

11. A urine collector comprising:
  a funnel body including,
    an upper funnel body with a handle extending outward from a top portion of the upper funnel body, a top opening bordered by a sloped sidewall and a first funnel hole, wherein the upper funnel body is configured to funnel a stream of urine from a subject through the top opening of the upper funnel body and along an interior surface of the upper funnel body toward and through the first funnel hole when the upper funnel body is upright, and
    a lower funnel body hingedly coupled to the upper funnel body having a second funnel hole, and
  a cup including an open mouth,
  wherein the cup is removably seated within the lower funnel hole.

12. The urine collector of claim 11 wherein the cup does not extend through the first funnel hole.

13. The urine collector of claim 11, wherein the upper funnel body and the lower funnel body are fabricated from a single sheet of paper.

14. The urine collector of claim 11, wherein the handle of the upper funnel body is hingedly coupled to the lower funnel body.

15. The urine collector of claim 11, wherein the upper funnel body includes a drain hole, wherein the drain hole is not obstructed by the lower funnel body.

16. A method of collecting urine sing the urine collector of claim 11 comprising directing urine into the upper funnel body, through the first funnel hole and the second funnel hole and into the cup, followed by pivoting the upper funnel body into an open position, followed by removing the cup from the lower funnel hole.

17. A urine collector comprising:
  a funnel body including an upper funnel body with a first funnel hole and a lower funnel body coupled to the upper funnel body, the lower funnel body including a second funnel hole,
  an open configuration adapted and arranged for loading a cup into the second funnel hole, and
  a closed configuration adapted and arranged for aligning the first funnel hole with the second funnel hole for directing urine received within the upper funnel body into the cup.

18. The urine collector of claim 17, wherein the first funnel hole has a diameter greater than a diameter of the second funnel hole.

19. The urine collector of claim 17, wherein the cup extends through the second funnel hole and not the first funnel hole.

20. A method of collecting urine sing the urine collector of claim 17 comprising directing urine into the upper funnel body, through the first funnel hole and the second funnel hole and into the cup, followed by pivoting the upper funnel body into the open configuration, followed by removing the cup from the lower funnel hole.

* * * * *